(12) United States Patent
Dyreby et al.

(10) Patent No.: US 7,832,927 B2
(45) Date of Patent: Nov. 16, 2010

(54) MANIPULATING SYSTEM, IN PARTICULAR A MANIPULATING SYSTEM FOR MANIPULATING AN X-RAY APPARATUS

(75) Inventors: Dick Daniel Dyreby, Silkeborg (DK); Mogens Soele Eriksen, Skanderborg (DK)

(73) Assignee: NRT—Nordisk Røntgen Teknik A/S, Hasselager (DK)

( * ) Notice: Subject to any disclaimer, the term of this patent is extended or adjusted under 35 U.S.C. 154(b) by 62 days.

(21) Appl. No.: 12/311,616

(22) PCT Filed: Oct. 8, 2007

(86) PCT No.: PCT/DK2007/000436

§ 371 (c)(1),
(2), (4) Date: May 8, 2009

(87) PCT Pub. No.: WO2008/040356

PCT Pub. Date: Apr. 10, 2008

(65) Prior Publication Data

US 2010/0014643 A1    Jan. 21, 2010

(30) Foreign Application Priority Data

Oct. 6, 2006  (DK) ................................ 2006 01297

(51) Int. Cl.
H05G 1/02 (2006.01)
(52) U.S. Cl. ....................................... 378/197; 378/194
(58) Field of Classification Search ................. 378/194, 378/196, 197
See application file for complete search history.

(56) References Cited

U.S. PATENT DOCUMENTS 4,435,830 A * 3/1984 Suzuki et al. ............... 378/197

(Continued)

FOREIGN PATENT DOCUMENTS

DE    2747583 A1    4/1979

(Continued)

*Primary Examiner*—Edward J Glick
*Assistant Examiner*—Thomas R Artman
(74) *Attorney, Agent, or Firm*—James Creighton Wray; Meera P. Narasimhan (57) ABSTRACT

A manipulating system, for manipulating two telescopic columns into desired positions in particular for use in an X-ray apparatus is disclosed, wherein the system comprises: one or more rails arranged in parallel in a first direction X and fastened to a ceiling; a carriage comprising an upper and a lower section, where said upper section comprises means for travelling along the rails in the X direction and the lower section is rotatable about an axis perpendicular to a horizontal X-Y plane by means of a rotation device arranged between the upper and lower section; —two sliding rails arranged in parallel with a mutual distance between the rails, provided in a lower face of the lower section, where the sliding rails overlap each other in the direction of the longitudinal extent of the sliding rails; —two telescopic columns extendable in a Z direction perpendicular to the X-Y plane, where each column is slidably fastened to separate. sliding rails in the lower section, and where the columns may slide past each other on the sliding rails; —connection means arranged in the free ends of the telescopic columns, where said connection means may be used in order to mount X-ray equipment, detectors, extension arms, vision systems and the like.

9 Claims, 5 Drawing Sheets

U.S. PATENT DOCUMENTS

| | | | |
|---|---|---|---|
| 6,155,713 A * | 12/2000 | Watanabe | 378/197 |
| 6,496,558 B2 * | 12/2002 | Graumann | 378/39 |
| 6,733,176 B2 * | 5/2004 | Schmitt | 378/196 |
| 6,872,000 B2 * | 3/2005 | Atzinger | 378/197 |
| 7,018,097 B2 * | 3/2006 | Schmitt | 378/197 |
| 7,073,939 B2 * | 7/2006 | Spahn | 378/196 |
| 7,641,391 B2 * | 1/2010 | Schwieker | 378/197 |
| 7,654,738 B2 * | 2/2010 | Fink et al. | 378/194 |
| 2003/0068008 A1 | 4/2003 | Schmitt | |
| 2003/0091151 A1 * | 5/2003 | Horbaschek et al. | 378/196 |
| 2003/0112926 A1 | 6/2003 | Atzinger | |
| 2004/0240609 A1 | 12/2004 | Spahn | |

FOREIGN PATENT DOCUMENTS

| | | |
|---|---|---|
| DE | 3218301 | 11/1983 |
| EP | 1306053 A2 | 5/2003 |
| WO | WO 2005/087105 A2 | 9/2005 |
| WO | WO 2006/095301 A1 | 9/2006 |

* cited by examiner

MANIPULATING SYSTEM, IN PARTICULAR A MANIPULATING SYSTEM FOR MANIPULATING AN X-RAY APPARATUS

This application claims the benefit of Danish Application No. PA 2006 01297 filed Oct. 6, 2006 and PCT/DK2007/000436 filed Oct. 8, 2007, which are hereby incorporated by reference in their entirety.

FIELD OF THE INVENTION

The present invention relates to a manipulating system for manipulating two telescopic columns into desired positions and an X-ray apparatus comprising such manipulating system where the columns of the manipulating system comprises means for holding an X-ray radiation source and an X-ray radiation receiver.

BACKGROUND OF THE INVENTION

In the art a number of systems exists which makes it possible to arrange an X-ray source in a proper position in relation to an X-ray radiation receiver, e.g. a detector. Examples of such systems are described in U.S. Pat. No. 4,435,830 and EP 1306053. In both these systems the radiation source and the radiation receiver are mounted on separate extendable telescopic columns where the columns are arranged in carriages, which carriages are suspended from a rail system comprising rails in a first direction on which rails, the telescopic column carriage may slide and which rails are attached to rails arranged perpendicularly to the first rails, so that the first rails may slide in relation to the second set of rails. By being able to move the telescopic column basis along the first set of rails the relative distance between the telescopic columns and thereby between the radiation source and the radiation receiver may be varied. By further sliding the telescopic column carriages and the first set of rails in relation to the second set of rails it is possible to position the radiation source and radiation receiver in a variation of desired relative positions.

From U.S. Pat. No. 6,872,000 B2 a system is disclosed, which improves the manoeuvrability of the prior art systems by introducing a rotary device in the construction. This construction comprises a first set of rails mounted in a ceiling in a first direction and a second set of rails perpendicular to the first set of rails and which second set of rails may slide in the first direction. The rotary device is mounted under the second set of rails and may slide in the longitudinal direction of the second set of rails. To the lower side of the rotary device a further rail is mounted on which rail two telescopic columns may slide in the longitudinal direction of the rail. At the distal ends of the telescopic columns, an X-ray radiation source and an X-ray receiver are mounted.

Although this apparatus provides added user-friendliness and increased possibilities in order to position the radiation source and the radiation receiver, the positioning system has a number of drawbacks. One such drawback is the limitation in positioning flexibility caused by the fact that the two telescopic columns are sliding in the same rail. Hereby examinations, where oblique projections in both directions longitudinally along the table are to be performed, are not possible.

Often it is desirable to perform x-ray images at an oblique angle, i.e. different from vertical, where the oblique angle is obtained by displacing the two columns relative to each other in both directions in the longitudinal direction of the patient, and angle the source so that the radiation direction is towards the detector.

To do such examinations with the system disclosed in U.S. Pat. No. 6,872,000 B2, is not possible. To perform X-ray images at an oblique angle is only possible at the end of the table and only in one direction longitudinally of the patient. Hereby only very limited patient coverage is obtained, e.g. either head or feet and oblique angulation is only possible in one direction. This is impractical for examinations where oblique projections longitudinally to the patient are required other than head and feet, and in particular for examinations where oblique projections from both sides longitudinally along the whole patient or sections remote from the feet and head are required.

In addition the orientation of the source must also be variable, such that for some images it is desirable to have the image surface perpendicular to the radiation direction, and in other examinations it is desirable to orientate the image surface horizontally, i.e. parallel to the patient to be examined. Usually such examinations are carried out from varying angles in order to examine the organ or body part as thoroughly as possible.

To do such examinations with the system disclosed in U.S. Pat. No. 6,872,000 B2, is not possible other than at the end of the table and only in one direction longitudinally of the patient. Hereby only very limited patient coverage is obtained, e.g. either head or feet and angulation of the detector is only possible in one direction. This is impractical for examinations where the image surface is desired to be perpendicular to the radiation direction.

In order to provide power, data and other control information to and from the radiation source and the radiation receiver it is necessary to provide cabling. Due to the extensive range of movement in the first and second sets of rails in the case of a system according to U.S. Pat. No. 6,872,000 B2, it is necessary to provide cabling, so that the cables will be long enough in order to accommodate the devices in the most extreme positions. That in turn implies that when the radiation source and radiation receiver are close together and the moving parts overall are close together, the cabling will be slack and have a tendency to hang or be curled in bundles. These bundles furthermore may become entangled in the moving parts of the device or require special installations in order to collect the surplus cabling in a manner where it does not interfere with the proper working of the device. Furthermore, excess cabling may also be a source of dust or dirt collection which is not very desirable in a surgery or medical environment.

SUMMARY OF THE INVENTION

It is therefore an object of the present invention to provide a simplified manipulation system, in particular for an X-ray examination apparatus which provides the user with an extended freedom to arrange the radiation source and radiation detector in any desired position and at the same time avoid the drawbacks of prior art devices.

This object is inventively achieved by a manipulation system according to the invention where the manipulation system, especially for manipulating two telescopic columns into desired positions, comprises one or more rails arranged in parallel in a first direction X in a X-Y plane;

a carriage comprising an upper and a lower section, where said upper section comprises means for travelling along the one or more rails in the X direction and the lower section is rotatable about an axis perpendicular to the X-Y plane by means of a rotation device arranged between the upper and lower section;

two sliding rails arranged in parallel with a mutual distance between the sliding rails, provided in a lower face of the lower section, where the sliding rails overlap each other in the direction of the longitudinal extent of the sliding rails;

two telescopic columns extendable in a Z direction, perpendicular to the X-Y plane, where each column is slidably fastened to separate sliding rails in the lower section, and where the columns may slide past each other on the sliding rails;

connection means arranged in the free ends of the telescopic columns, where said connection means may be used in order to mount X-ray equipment, detectors, extension columns, vision systems and the like.

The rails will facilitate movement in a first direction X. In order to provide movement in a Y direction, the two telescopic columns are slidably arranged in appropriate sliding means, e.g. rails provided in a carriage, which carriage may travel in the rails, for example arranged in the ceiling or wall in the first direction as discussed above. By rotating the lower section of the carriage in relation to the upper section, the telescopic columns will be able to be moved into any relative movement pattern and thereby the telescopic columns will be able to be positioned at any point within the reach of the slides provided in the lower section of the carriage and thereby also be displaced in the Y direction. It is in this connection foreseen that the lower section is able to turn through at least 330° in relation to the upper section, in order to cover substantially all practical positions used for X-ray examinations with this type of X-ray apparatus.

The overlap between the two sliding rails in the lower section of the carriage is provided so that the telescopic columns may pass each other, whereby it becomes possible to position the free end of the telescopic columns in any desired location within the reach of the carriage.

In a further advantageous embodiment of the invention, the manipulating system as described above is applied in an X-ray apparatus where the X-ray apparatus comprises an X-ray radiation source and an X-ray radiation receiver for receiving radiation from said radiation source, and where said manipulating system comprises:

one or more rails arranged in parallel in a first direction X and fastenable to a ceiling or wall;

a carriage comprising an upper and a lower section, where said upper section comprises means for travelling along the rails in the X direction and the lower section is rotatable about an axis perpendicular to the X-Y plane by means of a rotation device arranged between the upper and lower section;

two sliding rails arranged in parallel with a mutual distance between the rails, provided in a lower face of the lower section, where the sliding rails overlap each other in the direction of the longitudinal extent of the sliding rails;

two telescopic columns extendable in a Z direction perpendicular to the X-Y plane, where each column is slidably fastened to the sliding rails in the lower section, and where the columns may slide past each other on the sliding rails;

connection means arranged in the free ends of the telescopic columns, where said connection means in the end of a first telescopic column comprises means for holding said radiation receiver, and the connection means in the end of the second column comprises means for holding said radiation source.

In this manner, all the advantages of the manipulating system are transferred to an X-ray apparatus, so that a simplified movement system is provided, but with the added advantages of being able to position the radiation source and the radiation receiver in any desired location in relation to each other.

In the art it is important to be able to place the radiation source at the correct distance in relation to the radiation receiver in order to create the X-ray image of the desired body-part, and in order to create a sharpened, focused X-ray image. With the manipulating system incorporated in an X-ray apparatus it becomes possible to position the source and the receiver in any desired relationship to each other.

Furthermore, the cabling needed in order to provide power and input to the X-ray source and X-ray receiver as well as transferring information from these devices to a main computer or an image displaying unit may be arranged so that the cables are protected or hidden in the construction whereby the problem of having dust and dirt collecting bundles of cables and avoid a situation where the cabling interferes with the proper operation of the device may altogether be avoided.

In a further advantageous embodiment of the invention the cabling is arranged moveable in a cable enclosure, preferably a flexible cable enclosure, which is suspended along the one or more rails in the X-direction, and that a moveable cable enclosure guide is arranged to slide along the rails in the X-direction in response to the movement of the carriage. The preferably flexible cable enclosure comprising the cables is suspended along one of the rails in the X-direction, then leads the cable through the moveable cable enclosure guide, and on to the carriage, where the cable connects to components where cabling is required.

By arranging the cables in a flexible cable enclosure the cables are kept in an orderly fashion inside the rails, and due to the flexibility of the enclosure the cables are able to follow the carriage as it moves along the rails. The cables are kept inside the enclosure as opposed to prior art installations where the cables are suspended from hangers, whereby surplus cable will hang as loops underneath the rails. These loops may collect dirt, and may furthermore interfere with the equipment or other equipment and/or devices operated in the vicinity of the X-ray installation.

In a further advantageous embodiment of the invention, a cable management system is provided whereby the cabling may be arranged on a reel mechanism arranged in the lower section of the carriage so that as the telescopic columns extend or retract, the reel arranged in the lower section will make sure that any surplus cabling is wound onto the reels or as the columns are extended, the cabling will be unreeled from the reels. This further allows the X-ray source and/or the receiver to be detachable from the columns without disconnecting the cable.

In a still further advantageous embodiment of the invention the cable management system comprises three pulleys arranged for rotation around parallel axis, where the pulleys are provided with means for guiding a cable, and where said means on the three pulleys are arranged in a common plane, where the pulleys are arranged such that two pulleys are resiliently and oppositely biased mounted to the carriage on either side of the third pulley, which third pulley is mounted to a central translatable structure, to which structure also one end of the cable is mounted, whereby as the cable is unwound the two resiliently mounted pulleys will move towards each other, and as the cable is wound up, the pulleys will move apart, and as a device connected with the cable is moved horizontally the third pulley will move horizontally and the two other pulleys will compensate due to the resilient means, by moving correspondingly.

The distance between the pulleys as well as the resilient mounting means used for mounting the two outer pulleys determines the amount of cable available. By maintaining the pulleys as far apart as possible, due to the resilient means, slack is taken up, and at the same time the maximum length of cable is available. As the third pulley, arranged between the two outer pulleys moves, the tension in the cable in cooperation with the resilient means, such as springs, will move the pulleys correspondingly, providing a substantially constant tension in the cable, such that the user will not feel any extra or any less pull in the cable during movement of the third pulley—often caused by moving the entire cable management system along the rails used to move the apparatus along at.

The invention in a further embodiment provides the cable management system with two or more pulleys, where the pulleys are arranged for rotation around parallel axis, and that the pulleys are each provided with a threadlike groove corresponding in dimension to the cable, and that the distance between the pulleys may be varied, and further that one of the pulleys is resiliently biased away from the other pulley.

The cable is in this manner maintained in a condition without slack, in that the pulleys will function as cable storage and as cable is unwound the cable length will be delivered by the pulleys. The resiliently biased pulley, will at all times take up slack, and provide for a limited resistance during winding up and unwinding of cable.

In order to facilitate the integrated appearance of the overall apparatus the cable management system is arranged in the carriage, and that excess cable is provided in order to allow the x-ray source and/or the receiver to be detached from the columns, without disconnecting the cable.

This facilitates the possibility of avoiding loose hanging loops of cable and at the same time having surplus cable available on the pulleys such that when it is desirable to detach the X-ray receiver, this may be carried out without disconnecting the receiver, thereby making possible a number of examinations which would otherwise require different apparatus.

In a further advantageous embodiment the connection means in the end of said first column comprises first mounting means for rotating said radiation receiver around a vertical axis, and further second rotating means for rotating said receiver around a horizontal axis, and optionally that a telescopic link is arranged between said first mounting means and said second rotating means, whereby the first and second means may be translated linearly relative to each other.

Further the radiation receiver may be mounted rotatably around its own axis, i.e. an axis perpendicular to the radiation receiving plane, in order to rotate a non-square receiver relative to the patient in order to achieve optimum anatomical coverage.

Likewise, in a further advantageous embodiment the connecting means in the end of said second column comprises first mounting means for rotating said radiation source around a vertical axis, and further second rotating means for rotating said radiation source around a horizontal axis, and optionally that a telescopic link is arranged between said first mounting means and said second rotating means, whereby the first and second means may be translated linearly relative to each other.

By providing the multitude of movement and positioning possibilities in the end of the telescopic columns for the radiation receiver and/or the radiation source, it will be possible for users to manipulate the source and the receiver into any desired relative position of these two devices.

In a further advantageous embodiment of the invention the rails in the X-direction, may optionally be mounted in carriages that are sliding in rails in a Y-direction, perpendicular to the X-direction and which rails are fastened in a ceiling or wall. This is to allow the manipulating system to be parked or otherwise removed into a position in the surgery or medical room outside the area covered by the X direction.

DESCRIPTION OF THE DRAWING

Brief description of the drawing in which.

DETAILED DESCRIPTION OF A PREFERRED EMBODIMENT

Figure 1:
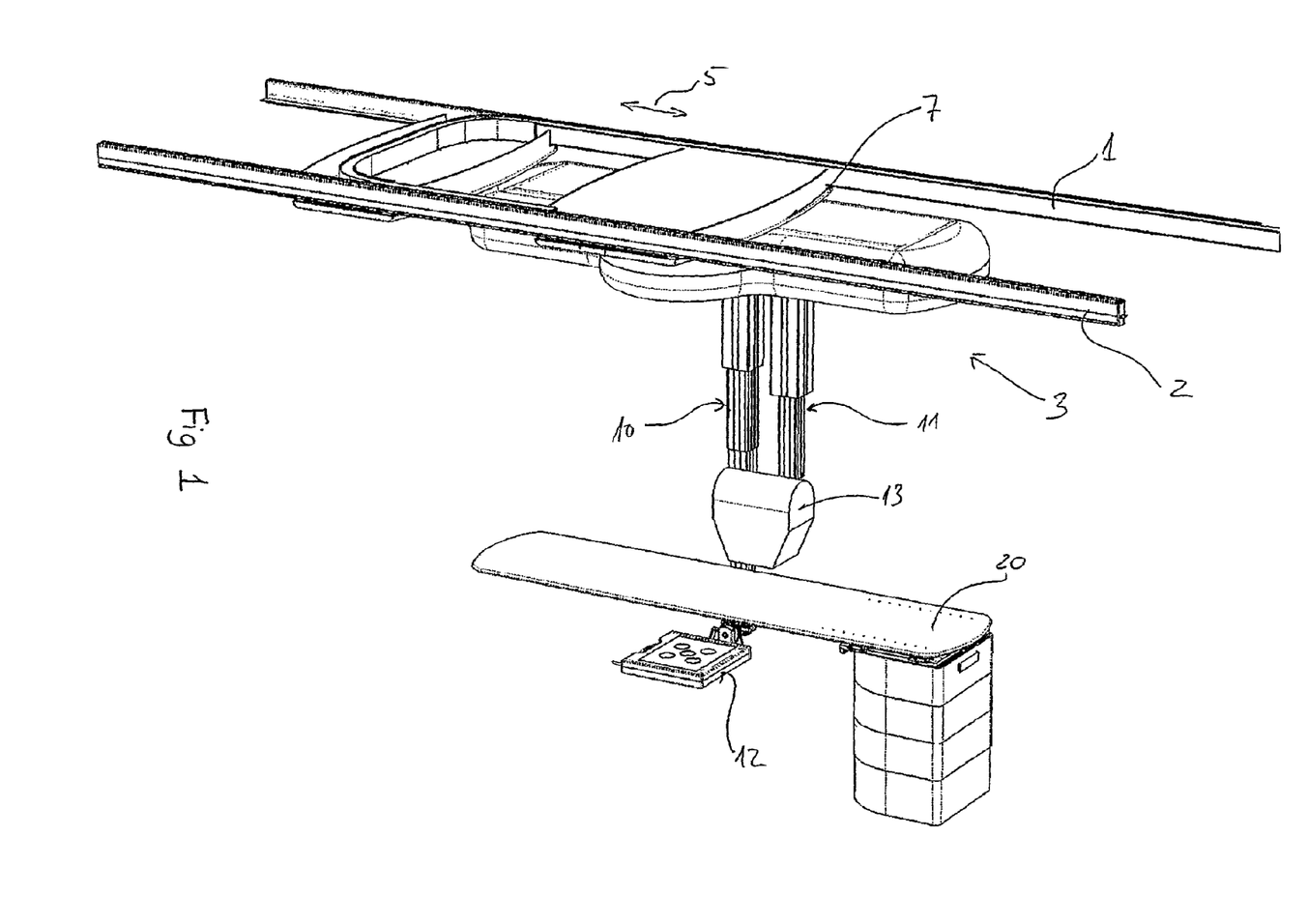
FIG. 1 illustrates an overall view of a preferred embodiment.
Figure 3:
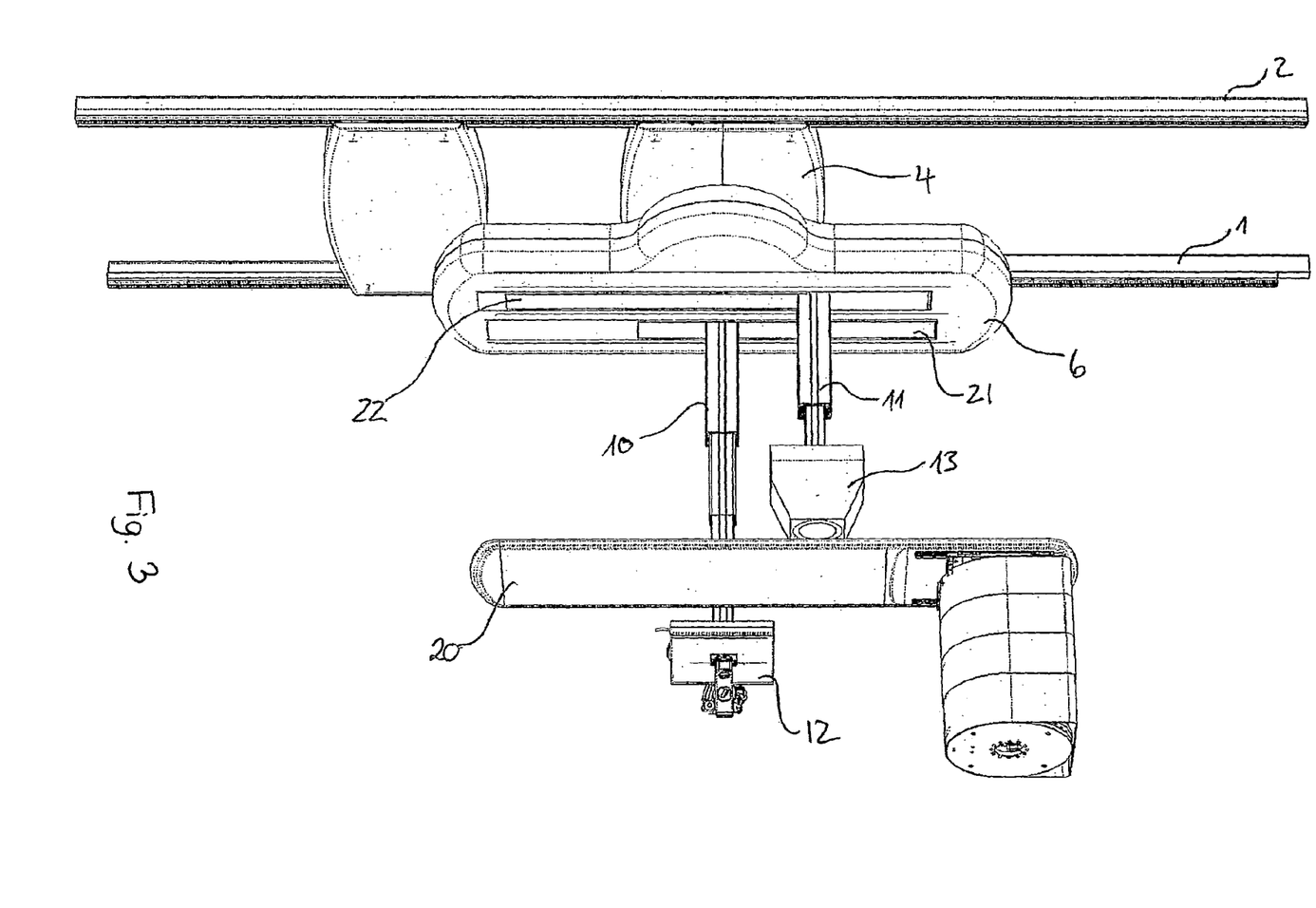

In FIGS. 1 and 3 it is illustrated how it is imagined that an apparatus according to the invention will be installed in a surgery or medical room. In the ceiling of the surgery or medical room are arranged two parallel rails 1, 2. A carriage 3 comprises means 4 for travelling along the rails 1, 2 in the direction indicated by the arrow 5. The means 4 will typically include rollers which rollers engage the rails 1 and at the same time propulsion means, e.g. in the shape of electric motors or the like.

The carriage 3 further comprises a lower section 6 connected to the upper section 4 by means of a rotatable unit 7. Two telescopic columns 10, 11 are slidably arranged in the lower section 6 of the carriage 3. The movement of the columns will be further explained with reference to FIGS. 2 and 3. At the distal end of the first telescopic column 10 an X-ray radiation receiver 12 is arranged. At the distal end of the second telescopic column 11 an X-ray radiation source 13 is mounted. As indicated in the figure the first telescopic column 10 is extended so that the X-ray radiation receiver 12 may be placed under e.g. a height adjustable patient examining table 20. The second telescopic column 11 is substantially completely retracted, but may be moved by extending the telescopic sections of the telescopic column into any desired height in relation to the X-ray radiation receiver 12. The two telescopic columns 10, 11 may furthermore be moved relatively to each other in slide rails (not shown) in the lower section 6.

Figure 2:
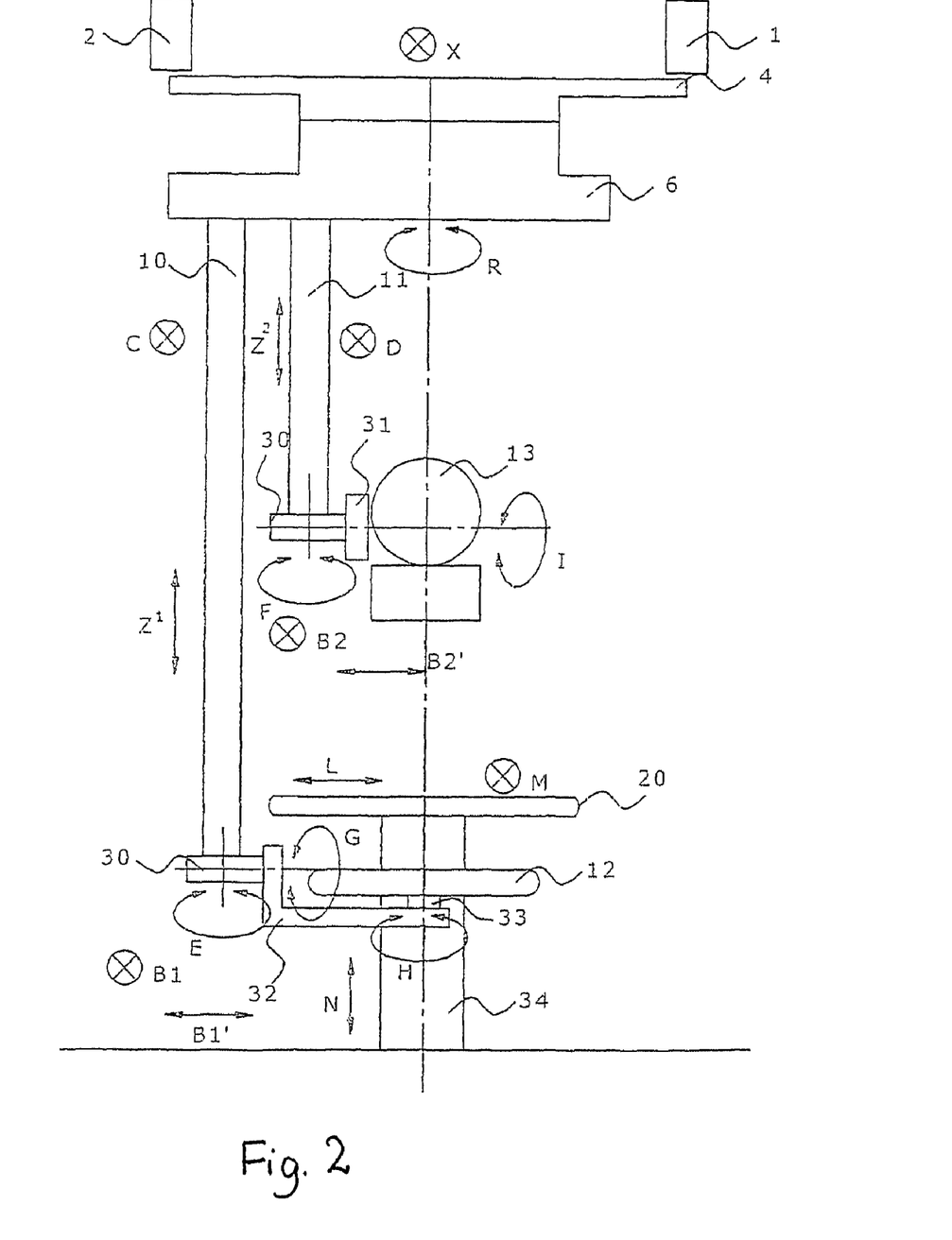
FIG. 2 illustrates the possible movement patterns of an X-ray apparatus according to the invention, and FIG. 3 provides an illustration of the device from below.

In FIG. 2 the lower section 6 two parallel slide rails 21, 22 are provided. The rails 21, 22 overlap in the direction of the travel direction as indicated by the arrows B1, B2. In this manner it is possible for the telescopic columns 10, 11 to change positions in the longitudinal direction of the slide rails 21, 22 which together with the rotational abilities as indicated by the arrow R of the lower section 6 in relation to the upper section 4 makes it possible to position the telescopic columns in substantially any relative relationship to each other.

Turning to FIG. 3 the features mentioned above are provided with the same reference numbers throughout the application.

In the lower section 6 the sliding rails may naturally have a further extent than what is illustrated, but in this particular embodiment the space from the end of a rail and to the exterior side of the lower section 6 is used in order to provide reels or other means for collecting the necessary cabling in order for the carriage, the telescopic columns and the two sections 4, 6 to be able to create the relative movements in order to position the X-ray radiation source 13 and X-ray radiation receiver 12 in desired positions.

In FIG. 2 all the movements of the inventive X-ray apparatus according to the invention are illustrated. The features are indicated by reference numbers, and the movements, i.e. the move patterns of each element of the invention are indicated by letters. The rails 1, 2 suitable to be fastened to either a ceiling or to walls or wall and ceiling make it possible for the carriage 3 to travel in the direction indicated by X, i.e. in or out of the plane of the figure. The upper section 4 of the carriage is connected to the lower section 6 by a rotary device, so that the lower section 6 may rotate as indicated by the arrow R in relation to the upper section 4 of the carriage 3.

The flexible columns 10, 11 may extend and retract as indicated by the arrows $Z_1$, $Z_2$ and furthermore they may slide in the slide rails 21, 22 arranged in the lower section 6 of the carriage in a direction indicated by the arrow B1, B2, i.e. in or out of the plane of the figure.

As the carriage 3 moves in the direction X, the telescopic columns 10, 11 will also move in the directions indicated by C and D.

The X-ray radiation source 13 attached to the distal end of the telescopic column 10 may further be rotated around a horizontal axis in the direction as indicated by the arrow F due to the arrangement of the suspension unit 30. The suspension unit may further comprise an extension possibility in a direction as indicated by the arrow B2' whereby the relative distance between the radiation source 13 and the telescopic column 11 may be altered. Furthermore, the radiation source may turn in the direction as indicated by the arrow I, i.e. around a horizontal axis, due to the provision of a turntable 31.

In a similar manner as described with reference to the radiation source, the radiation receiver 12 may also be manipulated in relation to the telescopic column 10. A suspension unit 30 disposed at the distal end of the telescopic column 10 comparable to the suspension unit 30 disposed at the end of the other telescopic column 11 may rotate the holder 32 for the radiation receiver 12 around both a vertical and a horizontal axis as indicated by the arrows E and G. Furthermore, the suspension unit 30 comprises means for translating the holder 32 along a horizontal axis in a direction indicated by the arrow B1'. The holder 32 may furthermore be designed in an L-shape, so that the surface of the radiation receiver may be at the same plane as the horizontal rotation axis of the suspension unit 30. This will facilitate the adjustment and the control of the adjustment, in particular the distance between the radiation source 13 and the radiation receiver 12 in order to create a focused and detailed X-ray image. Between the radiation receiver 12 and the holder 32 is a further rotation device 33 provided, whereby the receiver 12 may rotate in relation to the holder 32 as indicated by the arrow H. This enables optimum anatomical coverage if the receiver is not square.

Figure 4:
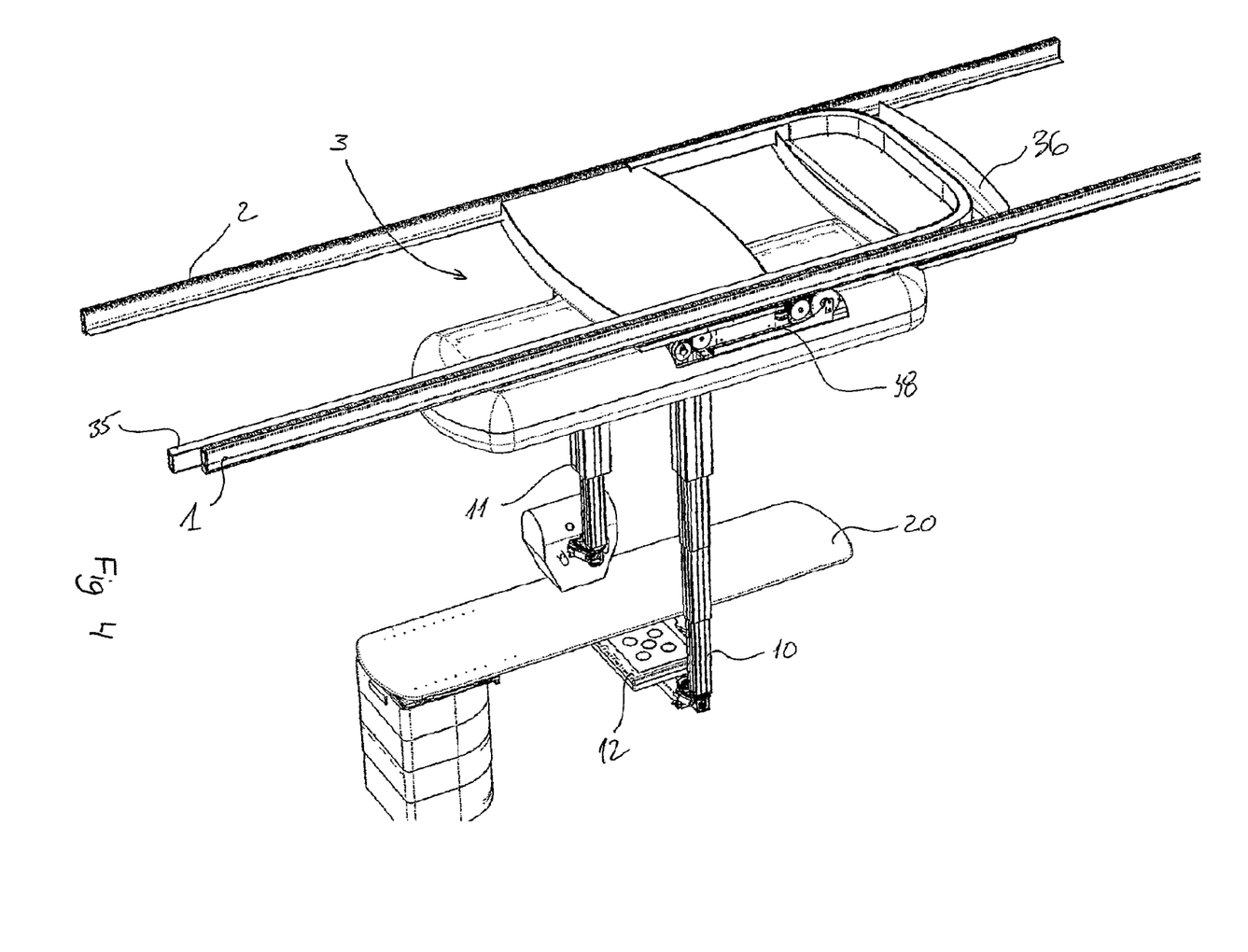
FIG. 4 illustrates the flexible cable enclosure and the moveable cable enclosure guide

In FIG. 4 is illustrated an example of the cable management system. The cables necessary for providing power, input etc for the X-ray apparatus, are assembled in a flexible cable enclosure 35 which is provided along part of one of the rails 1,2. A cable enclosure guide 36 is moveable along the rails 1,2 in response to the movement of the X-ray apparatus and carriage 3. As the carriage 3 moves along the rails the flexible cable enclosure 35 is guided by the cable enclosure guide 36, such that the flexible cable enclosure is more or less in contact with the rail 1,2 along which it is suspended. In one outer position of the carriage, where the carriage 3 is moved to the left in FIG. 4, the flexible cable enclosure will only be in contact with rail 1 over a short distance, but be in contact with rail 2 over a relatively long distance. In the opposite end, the flexible cable enclosure will almost exclusively be in contact with rail 1 and only slightly with rail 2.

Inside the lower section 6 of the carriage 3 a cable winch mechanism 38 is provided. This mechanism makes it possible to mechanically detach, for example the X-ray receiver from the column and manipulate it freely, in that a surplus length of cable is available by means of the cable management system 38.

The cable management system may comprise two or more pulleys arranged for rotation around parallel axis. Between their axles or attached to one or the other axle is arranged biasing means, such that the biasing means will urge the two axles, and thereby the pulleys apart. The pulleys are furthermore provided with grooves, such that as cable is wound around the pulleys this is done in an orderly fashion. As cable is unwound, when for example the X-ray receiver is detached from the column 10 the pulleys will rotate and at the same time the distance between the two axles will decrease. When the receiver again is mounted the pulleys, due to the tension in the biasing means will again rotate (in the opposite direction) and the axles will move apart, and thereby take up the slack in the cable. Although this mechanism has been exemplified with respect to the X-ray receiver, a similar mechanism may be implemented for any device where it is desirable to be able to extend the cable.

Although not within the scope of the present invention, the patient table 20 as illustrated in the figures may be translated in a direction indicated by M, i.e. in and out of the plane of the drawing, as well as across the base 34 of the table as indicated by the arrow L. The table may furthermore be height adjustable in the direction indicated by the arrow N by providing an extendable/retractable structure in the foundation 34 of the patient table 20.

Figure 5:
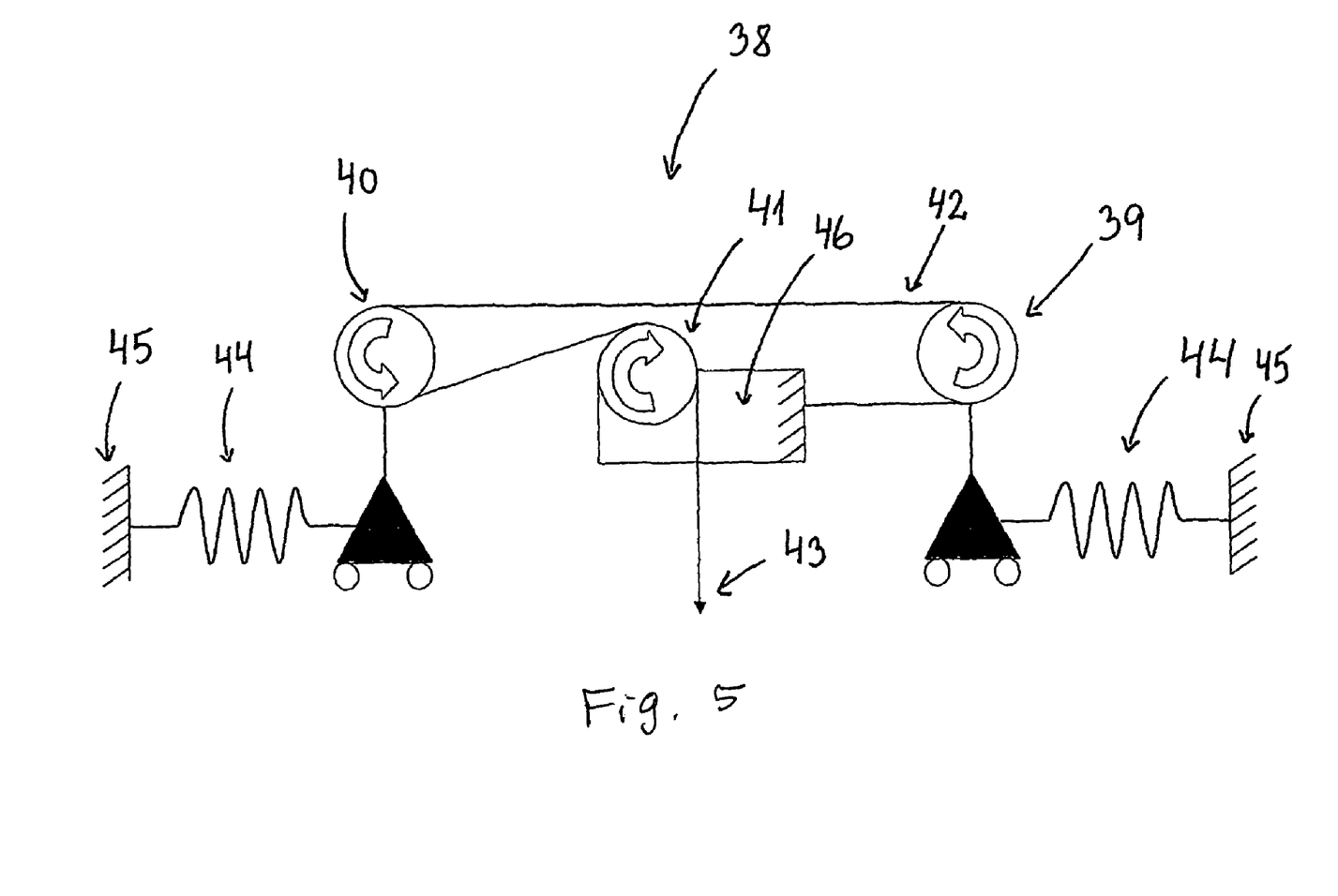
FIG. 5 illustrates an example of a cable management principle.

In FIG. 5 is illustrated one principle of the cable management system 38. Three pulleys 39,40,41 are provided and a cable 42 is wound around the pulleys in appropriate cable guide means (not illustrated). The free end 43 of the cable may be attached to for example an X-ray receiver or the like.

The two outer pulleys 39,40 are moveable in a horizontal direction. The movement is limited by resilient means, such as springs 44. The springs are mounted to the housing of the X-ray apparatus illustrated by 45. The end of the cable not being attached to for example an X-ray receiver is fastened to a moveable structure 46. On the same structure is the third pulley arranged. The structure may move horizontally.

As the free end of the cable, for example the X-ray receiver is displaced horizontally, the structure 46 will move correspondingly. Due to the pulleys 39,40 and the resilient means 44 the slack will be compensated. For example if the structure moves to the right in FIG. 5, the pulley 39 will rotate as indicated. At the same time the pulley due to the less tension in the cable will move under the influence of the spring 44 to the right. At the same time the pulley 40 will rotate as indicated and also move to the right due to the increased tension in the cable, provided by the movement of the structure and the spring opposite. The free end 43 of the cable will have neutral tension, i.e. it will move neither up nor down.

A comparable situation is of cause present with movement in the opposite direction.

In this manner a very versatile and yet easy to construct and manoeuvre device is provided by the novel and inventive apparatus according to the present invention.

The invention claimed is:

1. A manipulating system, for manipulating two telescopic columns into desired positions, wherein the system comprises:
   one or more rails arranged in parallel in a first direction X in an X-Y plane;
   a carriage comprising an upper and a lower section, where said upper section comprises means for travelling along the one or more rails in the X direction, and the lower section is rotatable about an axis perpendicular to the X-Y plane by means of a rotation device arranged between the upper and lower section;
   two sliding rails arranged in parallel with a mutual distance between the sliding rails, provided in a lower face of the lower section, where the sliding rails overlap each other in the direction of the longitudinal extent of the sliding rails;
   two telescopic columns extendable in a Z direction, perpendicular to the X-Y plane, where each column is slidably fastened to separate sliding rails in the lower section, and where the columns slide past each other on the sliding rails;
   connection means arranged in the free ends of the telescopic columns, where said connection means are capable of being used in order to mount X-ray equipment, detectors, extension arms and/or vision systems and the like.

2. An X-ray apparatus comprising a manipulating system, where said X-ray apparatus comprises an X-ray radiation source and an X-ray radiation receiver for receiving radiation from said radiation source, and where said manipulating system comprises:
   one or more rails arranged in parallel in a first horizontal direction X in an X-Y plane and fastenable to a ceiling or wall;
   a carriage, comprising an upper and a lower section, where said upper section comprises means for travelling along the rails in the X direction and the lower section is rotatable about an axis perpendicular to the horizontal X-Y plane by means of a rotation device arranged between the upper and lower section;
   two sliding rails arranged in parallel with a mutual distance between the rails, provided in a lower face of the lower section, where the sliding rails overlap each other in the direction of the longitudinal extent of the sliding rails;
   two telescopic columns extendable in a Z direction perpendicular to the X-Y plane, where each column is slidably fastened to the sliding rails in the lower section, and where the columns may slide past each other on the sliding rails;
   connection means arranged in the free ends of the telescopic columns, where said connection means in the end of a first telescopic column comprises means for holding said radiation receiver, and the connection means in the end of the second column comprises means for holding said radiation source.

3. An X-ray apparatus according to claim 2 wherein the connection means in the end of said first column comprises first mounting means for rotating said radiation receiver around a vertical axis, and further second rotating means for rotating said receiver around a horizontal axis, and optionally that a telescopic link is arranged between said first mounting means and said second rotating means, whereby the first and second means are translatable linearly relative to each other and optionally means for rotating said receiver around an axis perpendicular to the radiation receiving plane.

4. An X-ray apparatus according to claim 2 wherein the connection means in the end of said second column comprises first mounting means for rotating said radiation source around a vertical axis, and further second rotating means for rotating said radiation source around a horizontal axis, and optionally that a telescopic link is arranged between said first mounting means and said second rotating means, whereby the first and second means are translatable linearly relative to each other.

5. An x-ray apparatus according to claim 2, wherein a cable management system is provided, where said management system comprises a flexible cable enclosure, which is suspended along the one or more rails in the X-direction, and that a moveable cable enclosure guide is arranged to slide along the rails in the X-direction in response to the movement of the carriage and that the flexible cable enclosure comprising the cables is suspended along one of the rails in the X-direction, then leads the cable through the moveable cable enclosure guide, and on to the carriage, where the cable connects to components where cabling is required.

6. An X-ray apparatus according to claim 5 wherein the cable management system comprises two or more pulleys, where the pulleys are arranged for rotation around parallel axes, and that the pulleys are each provided with a groove corresponding in dimension to the cable, and that the distance between the pulleys may be varied, and further that one of the pulleys is resiliently biased away from the other pulley.

7. An X-ray apparatus according to claim 5, wherein the cable management system is arranged in the carriage, and that excess cable is provided in order to allow the x-ray source and/or the receiver to be detached from the columns, without disconnecting the cable.

8. An X-ray apparatus according to claim 5 wherein the cable management system comprises three pulleys arranged for rotation around parallel axes, where the pulleys are provided with means for guiding a cable, and where said means on the three pulleys are arranged in a common plane, where the pulleys are arranged such that two pulleys are resiliently and oppositely biased mounted to the carriage on either side of the third pulley, which third pulley is mounted to a central translatable structure, to which structure also one end of the cable is mounted, whereby as the cable is unwound the two resiliently mounted pulleys will move towards each other, and as the cable is wound up, the pulleys will move apart, and as a device connected with the cable is moved horizontally the third pulley will move horizontally and the two other pulleys will compensate due to the resilient means, by moving correspondingly.

9. An X-ray apparatus according to claim 2 wherein the one or more rails in the X-direction are mounted in carriages, which carriages slide in rails in a Y-direction, perpendicular to the X-direction and that are fastened in the ceiling or walls in order to allow parking of the manipulating system outside the area covered by the X-direction.

* * * * *